(12) United States Patent
Lin et al.

(10) Patent No.: US 6,207,717 B1
(45) Date of Patent: Mar. 27, 2001

(54) ENTRAPMENT OF VITAMINS WITH AN ELASTOMERIC SILICONE POLYETHER

(75) Inventors: Zuchen Lin; William James Schulz, Jr., both of Midland; Janet Mary Smith, Bay City, all of MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/228,301

(22) Filed: Jan. 12, 1999

(51) Int. Cl.[7] .................... A61K 47/30; A61K 7/00; A61K 7/48
(52) U.S. Cl. ............................................. 514/772.1
(58) Field of Search .................... 424/78.17, 70.12; 514/772.1

(56) References Cited

U.S. PATENT DOCUMENTS

| | | | |
|---|---|---|---|
| 3,920,805 | * 11/1975 | Roseman | 424/486 |
| 4,230,686 | * 10/1980 | Schopflin et al. | 424/486 |
| 5,364,633 | 11/1994 | Hill | 424/450 |
| 5,654,362 | 8/1997 | Schulz | 524/862 |
| 5,665,804 | 9/1997 | Hill | 524/268 |
| 5,811,487 | * 9/1998 | Schulz et al. | 424/486 |

FOREIGN PATENT DOCUMENTS

| | | |
|---|---|---|
| 440398 | 8/1991 | (EP) . |
| 631772 | 1/1995 | (EP) . |
| 832643 | 4/1998 | (EP) . |
| 9300085 | 1/1993 | (WO) . |

* cited by examiner

*Primary Examiner*—Peter F. Kulkosky
(74) *Attorney, Agent, or Firm*—James L. De Cesare

(57) ABSTRACT

Oil-soluble vitamins such as vitamin A and vitamin E can be entrapped in the oil phase of an elastomeric silicone polyether. The vitamin entrapped oil phase can then be emulsified and stabilized without requiring the use of other surfactants. The vitamin entrapped oil phase and water-in-oil emulsions prepared from the vitamin entrapped oil phase are useful in water-based skin and cosmetic compositions.

10 Claims, No Drawings

ENTRAPMENT OF VITAMINS WITH AN ELASTOMERIC SILICONE POLYETHER

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to entrapping vitamins with an elastomeric silicone polyether. In particular, oil-soluble vitamins such as vitamin A and vitamin E are delivered to substrates such as hair, skin, or the underarm, by entrapping the vitamin in the oil phase in the elastomeric silicone polyether.

BACKGROUND OF THE INVENTION

Natural and synthetic vitamins have been extensively used in various types of skin and cosmetic compositions. Although different methods have been proposed for entrapping and formulating vitamins into skin and cosmetic compositions, the known methods typically require the use of an anhydrous composition or a water-in-organic oil emulsion, both of which are greasy, and therefore cosmetically less appealing. In other instances, the known methods employ a very complicated stabilization system, when one desires to form a less greasy oil-in-water emulsion.

The present invention, in contrast, is based upon an elastomeric silicone polyether which can be used to entrap and formulate vitamins into skin and cosmetic compositions, and which can be used to form less greasy water-in-oil emulsions without requiring additional surfactants. This can be of considerable value in the personal care arena where skin sensitivity due to the presence of certain surfactants can be an issue. The method of making the vitamin entrapped compositions according to this invention is simple, and it does not require the use of high shear or heating. In addition, the elastomeric silicone polyether is capable of providing aesthetic benefits.

While U.S. Pat. 5,811,487 (Sep. 22, 1998), assigned to the same assignee as the present invention, broadly suggests that vitamins can be delivered with an elastomeric silicone polyether, the elastomeric silicone polyether in the '487 patent may contain anywhere from zero to 100 ethylene oxide (EO) units in its molecule. According to this present invention, however, it has been unexpectedly discovered that effective vitamin delivery can only be accomplished by using an elastomeric silicone polyether containing 4–30 (EO) units in its molecule. Moreover, in the case of vitamin A, there is required 7–30, rather than 4–30 (EO) units. This improved performance in a range within the range of the '487 patent is unexpected.

Furthermore, and according to this invention, it has also been unexpectedly discovered that effective vitamin delivery can only be accomplished by using an elastomeric silicone polyether prepared according to a method in which the equivalent ratio of the $\equiv$SiH in the $\equiv$SiH containing polysiloxane with polyether groups and the unsaturated hydrocarbon is 2:1 to 1:2. In contrast, the '487 patent employs an elastomeric silicone polyether prepared according to a method in which the equivalent ratio of the $\equiv$SiH in the $\equiv$SiH containing polysiloxane with polyether groups and the unsaturated hydrocarbon is 20:1 to 1:20. Again, improved performance in a range within the range of the '487 patent is unexpected.

In addition, nothing in the '487 patent suggests that oil-soluble vitamins such as vitamin A and vitamin E can be entrapped in the oil phase of elastomeric silicone polyethers.

BRIEF SUMMARY OF THE INVENTION

This invention relates to a method of making a vitamin enhanced silicone elastomer by entrapping a vitamin in an elastomeric silicone polyether. The vitamin is entrapped in the elastomeric silicone polyether by mixing the vitamin with the elastomeric silicone polyether. The elastomeric silicone polyether is a composition prepared by reacting (A) an $\equiv$Si—H containing polysiloxane and (B) a mono-alkenyl polyether in the presence of a platinum catalyst, until (C) an $\equiv$Si—H containing polysiloxane with polyether groups is formed. The $\equiv$Si—H containing polysiloxane with polyether groups (C) is then reacted with (D) an unsaturated hydrocarbon such as an alpha, omega-diene, an alpha, omega-diyne, or an alpha, omega-ene-yne, in the presence of (E) an oil and a platinum catalyst, until a silicone elastomer is formed by crosslinking and addition of $\equiv$SiH across double or triple bonds in the unsaturated hydrocarbon.

If desired, all of the reactants (i.e., the $\equiv$SiH containing siloxane(s), the mono-alkenyl polyether, the unsaturated hydrocarbon, the oil, and the platinum catalyst), can be combined and reacted in one pot, as described in copending U.S. patent application Ser. No. 08/866,993, filed Jun. 2, 1997, and assigned to the same assignee as the present application.

The invention also relates to a method of entrapping and delivering oil-soluble vitamins to a substrate using the elastomeric silicone polyether. Compositions according to the invention generally contain 0.01 to 50 percent by weight of a vitamin or a mixture of vitamins, 0.01 to 50 percent by weight of the elastomeric silicone polyether, with the balance of the composition being an oil.

Water-in-oil emulsions can be formed by using the composition as an oil phase. Thus, by adding water to the oil phase and shearing, water-in-oil emulsions can easily be manufactured. The entrapped vitamins remain in the oil phase after formation of the emulsion.

These elastomeric silicone polyether entrapped vitamins, as well as the water-in-oil silicone emulsions prepared using the elastomeric silicone polyether entrapped vitamins, are of value in treating substrates such as hair, skin, and the underarm areas of the human body.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

According to this invention, an elastomeric silicone polyether is used, and it can be prepared generally as depicted below:

Step 1: Incorporation of the polyether ≡SiH siloxane+
mono-alkenyl polyether +platinum catalyst→≡SiH
siloxane with polyether groups Step 2: Gelation ≡SiH siloxane with polyether group+
≡SiH siloxane (optional)+alpha, omega-diene+oil+
platinum catalyst→gel/elastomer Step 3: Shearing and swelling—Optional gel/elastomer+
oil+Vitamin→paste Step 4: Emulsification silicone gel/elastomer/paste+
water+vitamin+shear→silicone emulsion In Step 1, the molar ratio of the mono-alkenyl polyether to the ≡SiH in the ≡SiH siloxane should be between 0.9:1 to 1:12.

In Step 2, the ratio of the weight of the oil to the weight of the ≡SiH siloxane with polyether groups and the alpha, omega-diene can be from 1–98, but preferably is between 5–15. The equivalent ratio of the ≡SiH in the ≡SiH containing siloxane with polyether groups and the alpha, omega-diene can be from 2:1 to 1:2, but preferably is 1:1. While Step 2 can include a mixture of various types of compounds, at least one ≡SiH containing siloxane must include a polyether group.

For example, one formulation found especially suitable for Step 2 is a mixture containing the following compounds:

$Me_3SiO(Me_2SiO)_{50}[MeQSiO]_4(MeHSiO)_5SiMe_3$ $HSiMe_2O(Me_2SiO)_{10}SiHMe_2$ $Me_3SiO(Me_2SiO)_8(MeHSiO)_4SiMe_3$ 1,5-hexadiene, and decamethylcyclopentasiloxane. In these formulas, Me is methyl and Q is $-CH_2CH_2CH_2O(CH_2CH_2O)_{10}H$.

In Step 3, the silicone paste should contain 70–98 percent by weight of the oil. In Step 4, the weight ratio of water to the silicone paste can be 95:5 to 5:95.

The ≡Si—H containing polysiloxane is represented by compounds of the formula $R_3SiO(R'_2SiO)_a(R''HSiO)_bSiR_3$ referred to as type $A^1$, and compounds of the formula $HR_2SiO(R'_2SiO)_cSiR_2H$ or compounds of the formula $HR_2SiO(R'_2SiO)_a(R''HSiO)_bSiR_2H$ referred to as type $A^2$, including mixtures thereof. In the three formulas, R, R', and R", are alkyl groups with 1–6 carbon atoms; a is 0–250; b is 1–250; and c is 0–250. The molar ratio of compounds $A^2:A^1$ is 0–20, preferably 0–5. In preferred embodiments, compounds of types $A^1$ and $A^2$ are used in the reaction, however, it is possible to successfully conduct the reaction using only compounds of type $A^1$.

The ≡Si—H containing polysiloxane $A^1$ can also comprise an alkylhydrogen cyclosiloxane or an alkylhydrogen-dialkyl cyclosiloxane copolymer, represented in general by the formula $(R'_2SiO)_a(R''HSiO)_b$ where R', R", a, and b, are as defined above. Preferably, a is 0–7; and b is 3–10. Some representative compounds are $(OSiMeH)_4$, $(OSiMeH)_3(OSiMeC_6H_{13})$, $(OSiMeH)_2(OSiMeC_6H_{13})_2$, and $(OSiMeH)(OSiMeC_6H_{13})_3$, where Me is $-CH_3$.

The most preferred unsaturated hydrocarbon is an alpha, omega-diene of the formula $CH_2=CH(CH_2)_dCH=CH_2$ where d is 1–20. Some representative examples of suitable alpha, omega-dienes for use herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

However, other unsaturated hydrocarbons can be used such as alpha, omega-diynes of the formula $CH\equiv C(CH_2)_eC\equiv CH$; or alpha, omega-ene-ynes of the formula $CH_2=CH(CH_2)_eC\equiv CH$ where e is 0–20. Some representative examples of suitable alpha, omega-diynes for use herein are 1,3-butadiyne $HC\equiv C-C\equiv CH$ and 1,5-hexadiyne (dipropargyl) $HC\equiv C-CH_2CH_2-C\equiv CH$. One representative example of a suitable alpha, omega-ene-yne for use herein is hexene-5-yne-1 $CH_2=CHCH_2CH_2C\equiv CH$.

The reactions in Steps 1 and 2 requires a catalyst to effect the reaction between the ≡SiH containing siloxanes, the mono-alkenyl polyether, and the alpha, omega-diene. Suitable catalysts are Group VIII transition metals, i.e., the noble metals. Noble metal catalysts are described in U.S. Pat. No. 3,923,705, incorporated herein by reference. Another and preferred catalyst is Karstedt's catalyst, described in Karstedt's U.S. Pat. Nos. 3,715,334 and 3,814,730, incorporated herein by reference. Karstedt's catalyst is a platinum divinyl tetramethyl disiloxane complex, typically containing about one weight percent of platinum, carried in a polydimethylsiloxane fluid or in a solvent such as toluene.

The particular catalyst used in the examples was 20 µl and 200 µl portions of Karstedt catalyst as one weight percent of platinum carried in a two $mm^2/s$ polydimethylsiloxane fluid. Another preferred platinum catalyst is a reaction product of chloroplatinic acid and an organosilicon compound containing terminal aliphatic unsaturation. It is described in U.S. Pat. No. 3,419,593, incorporated herein by reference. The noble metal catalysts are used in amounts from 0.00001–0.5 parts per 100 weight parts of ≡SiH containing polysiloxane, preferably 0.00001–0.02 parts, most preferably 0.00001–0.002 parts.

The mono-alkenyl polyether is a compound of the formula $CH_2=CH(CH_2)_fO(CH_2CH_2O)_g(CH_2CH_3CHO)_hT$, or a compound of the formula $CH_2=CH-Q-O(CH_2CH_2O)_g(CH_2CH_3CHO)_hT$. In the formulas, T represents an end group which can be hydrogen; a C1–C10 alkyl group such as methyl, ethyl, propyl, butyl, and decyl; an aryl group such as phenyl; or a C1–C20 acyl group such as acetyl, propionyl, butyryl, lauroyl, myristoyl, and stearoyl. Q is a divalent linking group containing unsaturation such as phenylene $-C_6H_4-$. The value of f is 1–6; g has a value of 4–30; and h can be zero or have a value of 1–100.

It should be noted that for vitamin A derivatives, g should have a value of at least 7, i.e. 7–30 rather than 4–30.

The term oil as used herein is intended to include compounds containing a silicon atom such as (i) low molecular weight linear and cyclic volatile methyl siloxanes, (ii) low molecular weight linear and cyclic volatile and non-volatile alkyl and aryl siloxanes, and (iii) low molecular weight functional linear and cyclic siloxanes. Most preferred, however, are low molecular weight linear and cyclic volatile methyl siloxanes (VMS). Thus, this particular component constitutes what is shown as the "oil" in Step 2 of the process illustrated above.

VMS compounds correspond to the average unit formula $(CH_3)_jSiO_{(4-j)/2}$ in which j has an average value of two to three. The compounds contain siloxane units joined by ≡Si—O—Si≡ bonds. Representative units are monofunctional "M" units $(CH_3)_3SiO_{1/2}$ and difunctional "D" units $(CH_3)_2SiO_{2/2}$.

The presence of trifunctional "T" units $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear VMS have the formula $(CH_3)_3SiO\{(CH_3)_2SiO\}_kSi(CH_3)_3$. The value of k is 0–5. Cyclic VMS have the formula $\{(CH_3)_2SiO\}m$. The value of m is 3–9. Preferably, these volatile methyl siloxane have a boiling point less than about 250° C. and viscosity of about 0.65 to about 5.0 $mm^2/s$.

Representative linear volatile methyl siloxanes are hexamethyldisiloxane (MM) with a boiling point of 100° C., viscosity of 0.65 mm$^2$/s, and formula Me$_3$SiOSiMe$_3$; octamethyltrisiloxane (MDM) with a boiling point of 152° C., viscosity of 1.04 mm$^2$/s, and formula Me$_3$SiOMe$_2$SiOSiMe$_3$; decamethyltetrasiloxane (MD$_2$M) with a boiling point of 194° C., viscosity of 1.53 mm$^2$/s, and formula Me$_3$SiO(Me$_2$SiO)$_2$SiMe$_3$; dodecamethylpentasiloxane (MD$_3$M) with a boiling point of 229° C., viscosity of 2.06 mm$^2$/s, and formula Me$_3$SiO(Me$_2$SiO)$_3$SiMe$_3$; tetradecamethylhexasiloxane (MD$_4$M) with a boiling point of 245° C., viscosity of 2.63 mm$^2$/s, and formula Me$_3$SiO(Me$_2$SiO)$_4$SiMe$_3$; and hexadecamethylheptasiloxane (MD$_5$M) with a boiling point of 270° C., viscosity of 3.24 mm$^2$/s, and formula Me$_3$SiO(Me$_2$SiO)$_5$SiMe$_3$.

Representative cyclic volatile methyl siloxanes are hexamethylcyclotrisiloxane (D$_3$) a solid with a boiling point of 134° C. and formula {(Me$_2$)SiO}$_3$; octamethylcyclotetrasiloxane (D$_4$) with a boiling point of 176° C., viscosity of 2.3 mm$^2$/s, and formula {(Me$_2$)SiO}$_4$; decamethylcyclopentasiloxane (D$_5$) with a boiling point of 210° C., viscosity of 3.87 mm$^2$/s, and formula {(Me$_2$)SiO}$_5$; and dodecamethylcyclohexasiloxane (D$_6$) with a boiling point of 245° C., viscosity of 6.62 mm$^2$/s, and formula {(Me$_2$)SiO}$_6$.

Representative branched volatile methyl siloxanes are heptamethyl-3-{(trimethylsilyl)oxy}trisiloxane (M$_3$T) with a boiling point of 192° C., viscosity of 1.57 mm$^2$/s, and formula C$_{10}$H$_{30}$O$_3$Si$_4$; hexamethyl-3,3,bis {(trimethylsilyl)oxy} trisiloxane (M$_4$Q) with a boiling point of 222° C., viscosity of 2.86 mm$^2$/s, and formula C$_{12}$H$_{36}$O$_4$Si$_5$; and pentamethyl {(trimethylsilyl)oxy} cyclotrisiloxane (MD$_3$) with the formula C$_8$H$_{24}$O$_4$Si$_4$.

The invention also includes using low molecular weight linear and cyclic volatile and non-volatile alkyl and aryl siloxanes represented respectively by formulas R$_3$SiO (R$_2$SiO)$_n$SiR$_3$ and (R$_2$SiO)$_p$. R can be alkyl groups with 2–20 carbon atoms or aryl groups such as phenyl. The value of n is 0–80, preferably 5–20. The value of p is 3–9, preferably 4–6. These polysiloxanes have a viscosity generally in the range of about 1–100 mm$^2$/s.

Polysiloxanes can also be used where n has a value sufficient to provide siloxane polymers with a viscosity in the range of about 100–1,000 mm$^2$/sec. Typically, n can be about 80–375. Illustrative of such polysiloxanes are polydimethylsiloxane, polydiethylsiloxane, polymethylethylsiloxane, polymethylphenylsiloxane, and polydiphenylsiloxane.

Low molecular weight functional polysiloxanes can also be employed, and are represented by the formula R$_3$SiO (RQSiO)$_n$SiR$_3$ where Q is a functional group. Examples of such functional polysiloxanes containing functional groups represented by Q are acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, polyisobutylene (PIB) functional siloxane fluids, silanol functional siloxanes, and vinyl functional siloxane fluids.

The invention is not limited to using only low molecular weight polysiloxanes. Other types of oils can be used in Step 2 of the process. Thus, a single oil or a mixture of oils may be used.

The term oil is therefore expanded and intended to also encompass (i) organic compounds, (ii) the compounds containing a silicon atom as noted above, (iii) mixtures of organic compounds, (iv) mixtures of compounds containing a silicon atom, or (v) mixtures of organic compounds and compounds containing a silicon atom; which can be used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative compounds are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, VM&P solvent, and mineral spirits; alkyl halides such as chloroform, carbon tetrachloride, perchloroethylene, ethyl chloride, and chlorobenzene; aromatic hydrocarbons such as benzene, toluene, ethylbenzene, and xylene; esters such as ethyl acetate, isopropyl acetate, ethyl acetoacetate, amyl acetate, isobutyl isobutyrate, benzyl acetate, and isopropyl palmitate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

Other miscellaneous materials can also be used, such as acetonitrile, nitromethane, dimethylformamide, propylene oxide, trioctyl phosphate, butyrolactone, furfural, pine oil, turpentine, and m-creosol.

Further intended to be encompassed by the term oil are volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

In addition, the term oil is intended to include volatile fragrances such as natural products and perfume oils. Some representative natural products and perfume oils are ambergris, benzoin, civet, clove, leaf oil, jasmine, mate', mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

The term oil-soluble vitamin as used herein includes, but is not limited to, Vitamin Al, RETINOL, C$_2$–C$_{18}$ esters of RETINOL, vitamin E, TOCOPHEROL, esters of vitamin E, and mixtures thereof. RETINOL includes trans-RETINOL, 13-cis-RETINOL, 11-cis-RETINOL, 9-cis-RETINOL, and 3,4-didehydro-RETINOL. The vitamin can be used in the composition according to the invention in amounts of from 0.01 to about 50 percent by weight.

RETINOL, it should be noted, is an International Nomenclature Cosmetic Ingredient Name (INCI) designated by The Cosmetic, Toiletry, and Fragrance Association (CTFA), Washington DC, for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate, a product of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

Other materials may also be included in the compositions such as oil-soluble drugs. Representative examples of some suitable oil-soluble drugs which can be used are clonidine, scopolamine, propranolol, estradiol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Not to be excluded, and considered included herein as a drug for purposes of the present invention are antiacne agents such as benzoyl peroxide, triclosan, and tretinoin; antibacterial agents such as chlorohexadiene gluconate; antifungal agents such as miconazole nitrate; anti-inflammatory agents such as salicylic acid; corticosteroidal drugs; non-steroidal anti-inflammatory agents such as diclofenac; antipsoriasis agents such as clobetasol propionate and retinoids; anesthetic agents such as lidocaine; antipruritic agents; antidermatitis agents; and agents generally considered barrier films.

The process is carried out stepwise by combining the ≡SiH containing siloxane(s), the mono-alkenyl polyether, the alpha, omega-diene, the oil, and the platinum catalyst; and mixing these ingredients at room temperature until a gel, elastomer, paste, or emulsion, is formed. If desired, the gel, elastomer, paste, or emulsion, can be further diluted with an additional similar or dissimilar oil(s), to form the final composition. A blend of hexane and tetrahydrofuran, a fragrance, or a low molecular weight siloxane, are examples of oils that could be so employed. Higher temperatures to speed up the process can be used.

Additional amounts of oil can be added to the gel, i.e., Step 3, and the resulting mixture is subjected to shear force to form the paste. In Step 4, shear force is again used, during or after water is added to the paste to form the emulsion. Any type of mixing and shearing equipment may be used to perform these steps such as a batch mixer, planetary mixer, single or multiple screw extruder, dynamic or static mixer, colloid mill, homogenizer, sonolator, or a combination thereof.

Step 3 of the process is an optional step. However, if Step 3 is carried out, and an oil is included, the oil should be a material possessing the ability to solubilize the vitamin. Some suitable oils which possess this ability generally include silicone and hydrocarbon based oils. In addition, the oil should satisfy the melting point and the solubility requirements necessary for end uses being contemplated.

Typically, the process, i.e., Steps 1 and 2, is carried out using approximately a 1:1 equivalent ratio of the ≡Si—H in the ≡Si—H containing siloxane with polyether groups and the alpha, omega-diene. It is expected that useful materials may also be prepared by carrying out the process with an excess of either the ≡Si—H containing siloxane or the alpha, omega-diene, but this would be considered a less efficient use of the materials. The remainder of the composition comprises the oil, in amounts generally within the range of about 65–98 percent by weight of the composition, but preferably about 80–98 percent by weight.

The most preferred method for preparing compositions according to the invention includes the steps of (i) preparing an elastomeric silicone polyether at room temperature while mixing; (ii) if required, using an additional oil to solubilize the vitamin(s) by adding the vitamin(s) to the oil at room temperature while mixing; and (iii) adding the vitamin(s) containing oil slowly to the elastomeric silicone polyether at room temperature while mixing.

EXAMPLES

The following examples illustrate the invention in more detail. The elastomeric silicone polyether used in Examples 1–6 was prepared generally according to the procedure shown in detail in Example 1 of U.S. Pat. No. 5,811,487. In Examples 1–6, a reference to a numerical value for "g" refers to the "g" in the formula for the mono-alkenyl polyether used to prepare the elastomeric silicone polyether used in the example. As indicated above, it refers to a number which is representative of the ethylene oxide (EO) repeating units.

Example 1—Entrapment of Vitamin E 50 g of an elastomeric silicone polyether containing a 1:5 ratio of $(EO)_{12}$:crosslinks, i.e., g=12, was weighed into a beaker, and mixed with a mechanical mixer at 600 rpm. COVI-OX T-50, a vitamin E product of Henkel Corporation, La Grange, Ill., was added dropwise with a pipette, to the elastomeric silicone polyether. Upon initial contact with the vitamin E, the elastomeric silicone polyether became a clear, brown liquid. The addition of vitamin E to the elastomeric silicone polyether was continued until the degree of clarity lessened, at which point, the addition of the vitamin was stopped. A total of 19.24 g (27.8 percent of the overall weight), was added over a period of about 15 minutes. A uniform liquid was obtained. It was clear brown in color and very stable. The viscosity of the clear brown liquid was 91 $mm^2/s$.

Comparative Example 1

Using an alternative silicone elastomer with no (EO) substitution, and COVI-OX T-70, a vitamin E product also of Henkel Corporation, another sample was prepared according to the procedure in Example 1. The silicone elastomer corresponded generally to the type of elastomer prepared in Example 1 of U.S. Pat. No. 5,654,362 (Aug. 5, 1997). Upon initial contact with the vitamin-E, the silicone elastomer with no (EO) substitution did not become clear. Instead, vitamin-E clouded the silicone elastomer until only an opaque, brown liquid remained. A total of 12.52 g (20.0 percent of the overall weight), of vitamin E was added over about a 15 minute period. The brown liquid was unstable and began to separate after a few weeks. A thin but clear, dark brown layer rose to the top of the remaining cloudy brown liquid. This example shows the effect of omitting the monoalkenyl functionalized polyether group from the silicone elastomer.

Example 2—Entrapment of Vitamin E Acetate

The procedure in Example 1 was repeated, using an elastomeric silicone polyether with a 1:8 ratio of (EO)

$_7$:crosslinks, i.e., g=7, and vitamin E acetate, a product of Roche Vitamins & Fine Chemicals, Nutley, N.J. As in Example 1, the sample reached a level of clarity upon contact with the vitamin E acetate. A total of 7.48 g (13.0 percent of the overall weight), of vitamin E acetate, was added over a period of about 10 minutes. The resulting liquid had a slight, white haze, but was otherwise colorless.

Example 3—Entrapment of Vitamin A Acetate 50 g of an elastomeric silicone polyether with a 1:5 ratio of $(EO)_{12}$:crosslinks, i.e., g=12, was weighed into a beaker, and mixed with a mechanical mixer at 600 rpm. Vitamin A Acetate, a product of Fluka Chemie AG, Buchs, Switzerland, was added dropwise with a pipette to the elastomeric silicone polyether. Upon initial contact with the vitamin A acetate, the elastomeric silicone polyether became a clear, yellow liquid. The addition of vitamin A acetate to the elastomeric silicone polyether was continued until the degree of clarity lessened, at which point addition of the vitamin was stopped. A total of 20.92 g (29.5 percent of the overall weight), of vitamin A acetate was added over a period of about 10 minutes. The resulting material was a clear, yellow liquid, that became hazy over a period of a few weeks. It had a viscosity of 50 mm$^2$/s.

Comparative Example 2

Using an elastomeric silicone polyether with a 1:12 ratio of $(EO)_4$:crosslinks, i.e., g=4, and vitamin A acetate of Fluka Chemie AG, another sample was prepared according to the procedure used in Example 2. A total of 6.98 g (12.2 percent of the overall weight), of vitamin A acetate was added over about a 10 minute period. The resulting material became hazy, and it separated over a period of a few weeks. On the surface of the material was observed a bright yellow cream, which covered the remainder of the material, which was a hazy, yellow gel. This example shows the effect of using an elastomeric silicone polyether with a polyether chain length which is not of an adequate length for effectively entrapping vitamin A acetate. As can be seen in Example 2, by way of comparison, vitamin A acetate was effectively entrapped in the elastomeric silicone polyether when the polyether chain length was about 7

Example 4—Entrapment of Vitamin A Acetate and Vitamin E 50 g of an elastomeric silicone polyether with a 1:5 ratio of $(EO)_{12}$:crosslinks, i.e., g=12, was weighed into a beaker, and mixed with a mechanical mixer at 600 rpm. Using a pipette, there was added to the elastomeric silicone polyether, a 1:1 weight/weight solution containing COVI-OX T-50 vitamin E of Henkel Corporation and vitamin A acetate of Fluka Chemie AG. Upon initial contact with the solution, the elastomeric silicone polyether became a clear, yellow-green liquid. The addition of the vitamin solution to the elastomeric silicone polyether was continued until the degree of clarity lessened, at which point addition was discontinued. A total of 9.68 g (16.2 percent of the overall weight), of the solution was added over a period of about 10 minutes. The result material was a slightly hazy, yellow-green liquid that was stable at room temperature.

Example 5—Water-In-Oil Emulsion Lotion with Vitamin A Acetate 10 g of isopropyl palmitate was added to 10 g of an elastomeric silicone polyether with a 1:12 ratio of (EO)$_{12}$:crosslinks, i.e., g=12, and mixed with a mechanical mixer at 300 rpm. An emulsion was prepared using this solution by increasing the rpm to 600, and then slowly adding 77.78 g of deionized water with a pipette over a period of about 20 minutes. As the emulsion was being mixed, 7.5 g of vitamin A acetate of Fluka Chemie AG was added. The emulsion was pale yellow with a composition that included about 73.9 percent by weight of water and 7.1 percent by weight of vitamin A acetate. The remainder of the composition to 100 percent was the elastomeric silicone polyether. About 49.3 g of the emulsion was then mixed with 8 g of decamethylcyclopentasiloxane, 2 g of a 1,000 mm$^2$/s polydimethylsiloxane fluid, and 2.14 g of the same elastomeric silicone polyether used initially in this example. An additional 36.44 g of deionized water was added slowly over about 10 minutes. During addition of water, the rpm was increased from 300 to 600 rpm in increments of 100. When the addition of water was complete, the lotion was stirred for an additional 15 minutes at 600 rpm. The resulting water-in-oil emulsion lotion was opaque, pale yellow in appearance, and stable at room temperature.

Example 6—Water-In-Oil Emulsion Lotion with Vitamin E 15 g of an elastomeric silicone polyether with a 1:5 ratio of $(EO)_{12}$:crosslinks, i.e., g=12, was mixed with 6 g of decamethylcyclopentasiloxane, 1.5 g of a 1,000 mm$^2$/s polydimethylsiloxane fluid, and 2.5 g of COVI-OX T-50 vitamin E of Henkel Corporation, using a mechanical mixer at 300 rpm for 10 minutes. This step produced an oil phase. About 75 g of deionized water was added to the oil phase with a pipette over a period of about 10 minutes. During addition of the water, the rpm was increased from 300 to 600 rpm in increments of 100. When addition of water was complete, the lotion was stirred for an additional period of about 15 minutes at 600 rpm. The resulting water-in-oil emulsion lotion was an off-white cream that had a tan tint. It was quite smooth and stable.

While elastomeric silicone polyethers prepared according to the '487 patent are most preferred for use according to this invention, other types of elastomeric silicone polyethers may be employed herein, without departing from this invention.

For example, one type of elastomeric silicone polyether which can be used is one prepared by reacting a mono-alkenyl polyether with the following two types of organosilicon monomers:

ZMe$_2$SiO(Me$_2$SiO)$_r$(MeHSiO)$_s$SiMe$_2$Z and

QMe$_2$SiO(Me$_2$SiO)$_t$(MeQSiO)$_u$SiMe$_2$Q where Me is methyl; Z is CH$_3$ or H provided there are at least two H atoms per molecule; Q is vinyl or another alpha-unsaturated alkenyl group or CH$_3$ provided there are at least two carbon-carbon double bonds per molecule; r is 0–1,000; s is 0–100; t is 0–1,000; and u is 0–100

Another type of elastomeric silicone polyether which can be used includes those types prepared by reacting the mono-alkenyl polyether with the following two other types of organosilicon monomers:

(RMe$_2$SiO$_{1/2}$)$_v$(SiO$_{4/2}$)$_w$(RSiO$_{3/2}$)$_x$(RMeSiO$_{2/2}$)$_y$ and QMe$_2$SiO(Me$_2$SiO)$_z$(MeQSiO)$_\lambda$SiMe$_2$Q where Me is methyl; R is methyl or H provided there are at least two H atoms per molecule; Q is vinyl or another alpha-unsaturated alkenyl group or methyl provided there are at least two carbon-carbon double bonds per molecule;

v is 2–50; w is 0–20; x is 0–50; y is 0–1,000; z is 0–1,000; and λ is 0–100.

Example 7 below shows a process for making this latter type of elastomeric silicone polyether.

Example 7

In this example, an ESCO EL-1 processor mixer was employed. The processor mixer was equipped with a one liter jacketed glass container having a heating and a cooling capability, an anchor sweep blade with speed control settings of 20–300 rpm, a high speed homogenizer with Cowles type blades and speed controls for 750–15,000 rpm operations, a temperature gauge, a product inlet, a vacuum connection, and a circulation bath with a heating and a cooling capacity. The raw materials and amounts used for preparing the elastomeric silicone polyethers were 0.09 percent by weight of tetrakis(dimethylsiloxy)silane of the formula $Si[OSi(CH_3)_2H]_4$; 9.75 percent by weight of a vinyl terminated polydimethylsiloxane with approximately 300 dimethylsiloxy units in the molecule; 0.16 percent by weight of a mono-alkenyl polyether of the type $CH_2=CH(CH_2)_yO(CH_2CH_2O)_g(CH_2CH_3CHO)_hT$ where T was H; 90 percent by weight of decamethylcyclopentasiloxane; and 0.19 percent by weight of Karstedt's catalyst, a platinum divinyl tetramethyl disiloxane complex containing about one weight percent of platinum. The first step in the manufacture of the elastomeric silicone polyether was to add to the ESCO mixer tetrakis(dimethylsiloxy)silane, the mono-alkenyl polyether, and about 80 percent by weight of decamethylcyclopentasiloxane. After loading the materials into the ESCO mixer, the mixer was closed. Heating of the mixer was initiated by setting the circulatory bath set point to 50° C. The sweep blade of the mixer was activated to about 20 percent of its capacity, and the homogenizer of the mixer was activated to about 5 percent of its capacity. The platinum catalyst was added to the ESCO mixer by means of a syringe through a port hole in the mixer, and the timer was started. Mixing was continued for about one hour. The vinyl terminated polydimethylsiloxane was weighed into a beaker. It was added to the ESCO mixer by removing the inlet plug. This addition was followed by addition to the ESCO mixer of the remainder of the decamethylcyclopentasiloxane. The inlet was closed and the timer was restarted. The speed of the homogenizer was increased to about 10 percent of its capacity. The fluid in the mixer began to thicken and gel, and it began to move up the mixer shaft. Mixing was continued but the speed of the homogenizer was increased to 20–25 percent of its capacity, and the scraper in the mixer was set at 20–25 percent of its capacity. The total of the mix time measured from the point of addition of the vinyl terminated polydimethylsiloxane was about 2.5 to 3 hours at 50° C. After the elapse of that time, the mixer set point was lowered to about 25° C., and mixing was continued until the product had cooled to about 30° C. The mixer was then stopped, and the sample in the mixer was removed.

Example 8—Entrapment of Vitamin E and Vitamin A Acetate 50 g of the elastomeric silicone polyether prepared above in Example 7 was weighed into a glass beaker and mixed with a mechanical mixer at 600 rpm. A pre-made mixture containing equal portions of COVI-OX T-50 vitamin E of Henkel Corporation and vitamin A acetate of Fluka Chemie AG, was added to the elastomeric silicone polyether over a period of about 10 minutes. A total of 5.85 g (10.5 percent of the overall weight), of the vitamin mixture was added. The resulting material was a hazy, yellow-green syrup with good stability.

The silicone elastomer, silicone gel, silicone paste, and silicone emulsion of this invention have particular value in the personal care arena. Because of the unique volatility characteristics of the VMS component of these compositions, they can be used alone, or blended with other cosmetic fluids, to form a variety of over-the-counter (OTC) personal care products.

Thus, they are useful as carriers in antiperspirants and deodorants, since they leave a dry feel, and do not cool the skin upon evaporation. They are lubricious and improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss and drying time, and provide conditioning benefits.

In cosmetics, they function as leveling and spreading agents for pigments in make-ups, color cosmetics, foundations, blushes, lipsticks, lip balms, eyeliners, mascaras, oil removers, color cosmetic removers, and powders. When incorporated into sticks, gels, lotions, aerosols, and roll-ons, the compositions impart a dry, silky-smooth, payout.

In addition, the compositions exhibit other advantageous and beneficial properties such as clarity, shelf stability, and ease of preparation. Hence, they can have wide application, but especially in antiperspirants, deodorants, in perfumes as a carrier, and for conditioning hair.

The silicone elastomers, gels, pastes, and emulsions, have uses beyond the personal care arena, however, including their use as a filler or insulation material for electrical cable, a soil or water barrier for in-ground stabilization, or as a replacement for epoxy materials used in coil-on-plug designs in the electronics industry.

They are also useful as carrier for crosslinked silicone rubber particles. In that application, (i) they allow ease of incorporation of the particles into such silicone or organic phases as sealants, paints, coatings, greases, adhesives, antifoams, and potting compounds; and (ii) they provide for modifying Theological, physical, or energy absorbing properties of such phases in either their neat or finished condition.

In addition, the silicone elastomers, gels, pastes, and emulsions, are capable of functioning as carriers for biocides, herbicides, pesticides, and other biologically active substances; and they can be used to incorporate water and water-soluble substances into hydrophobic systems. Examples of some watersoluble substances are glycerol, enzymes, and glycolic acid.

Where barrier films are required, the silicone elastomers, gels, pastes, and emulsions, can be applied to the surface of a substrate, such that when the oil component is allowed to evaporate, it leaves behind a fine powder-like particulate film on the surface of the substrate.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of making a vitamin enhanced silicone elastomer comprising entrapping an effective amount of a vitamin in a silicone elastomer by mixing the vitamin with the silicone elastomer, the silicone elastomer being prepared by a method comprising reacting:

(A) an ≡Si—H containing polysiloxane of the formula $R_3SiO(R'_2SiO)_a(R''HSiO)_bSiR_3$ or the formula $(R'_2SiO)_a(R''HSiO)_b$, and optionally an ≡Si—H containing polysiloxane of the formula $HR_2SiO(R'_2SiO)_cSiR_2H$ or an ≡Si—H containing polysiloxane of the formula $HR_2SiO(R'_2SiO)_a(R''HSiO)_bSiR_2H$, where R, R', and R'' are alkyl groups with 1–6 carbon atoms, a is 0–250, b is 1–250, and c is 0–250; and (B) a mono-alkenyl polyether of the formula $CH_2=CH(CH_2)_fO(CH_2CH_2O)_g(CH_2CH_3CHO)_hT$, or the formula $CH_2=CH-Q-O(CH_2CH_2O)_g(CH_2CH_3CHO)_hT$, where T is hydrogen, a $C_1$–$C_{10}$ alkyl group, an aryl group, or a $C_1$–$C_{20}$ acyl group; Q is a divalent linking group containing unsaturation; f is 1–6, g is 4–30; and h is zero or 1–100; in the presence of a platinum catalyst, until an ≡Si—H containing polysiloxane with polyether groups is formed; and reacting:

(C) the ≡Si—H containing polysiloxane with polyether groups; and (D) an unsaturated hydrocarbon selected from the group consisting of alpha, omega-dienes of the formula $CH_2=CH(CH_2)_dCH=CH_2$, alpha, omega-diynes of the formula $CH≡C(CH_2)_eC≡CH$, and alpha, omega-ene-ynes of the formula $CH_2=CH(CH_2)_eC≡CH$, where d and e are 1–20; in the presence of (E) an oil selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; and in the presence of a platinum catalyst, until a silicone elastomer is formed by crosslinking and addition of ≡SiH across double or triple bonds in the unsaturated hydrocarbon; the equivalent ratio of the ≡SiH in the ≡SiH containing polysiloxane with polyether groups and the unsaturated hydrocarbon being 2:1 to 1:2.

2. A method according to claim 1 including the further steps of adding additional amounts of oil to the silicone elastomer, and shearing the oil and silicone elastomer until a silicone paste is formed.

3. A method according to claim 2 including the further steps of adding water to the silicone paste, and shearing the water and silicone paste until a silicone emulsion is formed.

4. A method according to claim 3 in which the silicone emulsion is formed free of the presence of a surfactant.

5. A method according to claim 1 in which the second step includes as an additional reactant (F) an ≡Si—H containing polysiloxane of the formula $R_3SiO(R'_2SiO)_a(R''HSiO)_bSiR_3$ or the formula $(R'_2SiO)_a(R''HSiO)_b$, and optionally an ≡Si—H containing polysiloxane of the formula $HR_2SiO(R'_2SiO)_cSiR_2H$ or an ≡Si—H containing polysiloxane of the formula $HR_2SiO(R'_2SiO)_a(R''HSiO)_bSiR_2H$, where R, R', and R'' are alkyl groups with 1–6 carbon atoms, a is 0–250, b is 1–250, and c is 0–250.

6. A method according to claim 1 in which the oil is a linear volatile methyl siloxane of the formula $(CH_3)_3SiO\{(CH_3)_2SiO\}_kSi(CH_3)_3$ where k is 0–5, or a cyclic volatile methyl siloxane of the formula $\{(CH_3)_2SiO\}_m$ where m is 3–8, the volatile methyl siloxane have a boiling point less than about 250° C. and a viscosity of 0.65–5.0 mm²/s.

7. A method according to claim 1 in which the molar ratio of the mono-alkenyl polyether to ≡SiH in the ≡SiH containing polysiloxane is between 0.9:1 and 1:12.

8. A method according to claim 1 in which the vitamin is present in combination with an oil-soluble drug.

9. A silicone elastomer composition prepared according to the method defined in claim 8.

10. A method of treating hair, skin, or the underarm comprising applying to the hair, skin, or the underarm, the silicone elastomer composition of claim 9.

* * * * *